United States Patent
Engel et al.

(10) Patent No.: US 10,648,930 B2
(45) Date of Patent: May 12, 2020

(54) APPARATUS FOR DETERMINING AN EFFECTIVE ENERGY SPECTRUM OF AN X-RAY TUBE

(71) Applicant: KONINKLIJKE PHILIPS N.V., Eindhoven (NL)

(72) Inventors: Klaus Jürgen Engel, Veldhoven (NL); Gereon Vogtmeier, Aachen (DE); Rolf Karl Otto Behling, Norderstedt (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 152 days.

(21) Appl. No.: 15/780,992

(22) PCT Filed: Dec. 2, 2016

(86) PCT No.: PCT/EP2016/079646
§ 371 (c)(1),
(2) Date: Jun. 1, 2018

(87) PCT Pub. No.: WO2017/093520
PCT Pub. Date: Jun. 8, 2017

(65) Prior Publication Data
US 2018/0328865 A1    Nov. 15, 2018

(30) Foreign Application Priority Data
Dec. 3, 2015  (EP) .................................. 15197709

(51) Int. Cl.
*G01N 23/046*  (2018.01)
*A61B 6/03*  (2006.01)
*A61B 6/00*  (2006.01)

(52) U.S. Cl.
CPC .......... *G01N 23/046* (2013.01); *A61B 6/032* (2013.01); *A61B 6/42* (2013.01); *A61B 6/482* (2013.01); *G01N 2223/419* (2013.01); *G01N 2223/423* (2013.01)

(58) Field of Classification Search
None
See application file for complete search history.

(56) References Cited

U.S. PATENT DOCUMENTS

| | | |
|---|---|---|
| 2011/0121163 A1 | 5/2011 | Kang |
| 2014/0014828 A1 | 1/2014 | Bredno |
| 2014/0233694 A1 | 8/2014 | Wang |
| 2016/0022243 A1 | 1/2016 | Nakai |

FOREIGN PATENT DOCUMENTS

| | | |
|---|---|---|
| WO | 2007057841 A2 | 5/2007 |
| WO | 2008072175 A1 | 6/2008 |
| WO | 2014205423 A1 | 12/2014 |

*Primary Examiner* — Yara B Green
(74) *Attorney, Agent, or Firm* — Larry Liberchuk (57) ABSTRACT

The present invention relates to an apparatus for determining an effective energy spectrum of an X-ray tube. It is described to provide (210) a temporally varying acceleration voltage of an X-ray tube for a time period. A temporally varying X-ray tube current is also provided (220) for the time period. At least one product of the temporally varying X-ray tube current and a time interval is determined (230). An effective energy spectrum of the X-ray tube processing the X-ray tube is determined (250) as a function of the at least one product of the temporally varying X-ray tube current and the time interval and as a function of the voltage of the X-ray tube.

11 Claims, 5 Drawing Sheets

APPARATUS FOR DETERMINING AN EFFECTIVE ENERGY SPECTRUM OF AN X-RAY TUBE

FIELD OF THE INVENTION

The present invention relates to an apparatus for determining an effective energy spectrum of an X-ray tube, to a system for determining object related quantities based on X-ray image data, to a method for determining an effective energy spectrum of an X-ray tube, and to a method for determining an object related quantity based on X-ray image data, as well as to a computer program element and a computer readable medium.

BACKGROUND OF THE INVENTION

The next generation of X-ray imaging is seeing "X-ray colours" with spectrally sensitive detectors being used in acquiring images, as compared to the traditional "greyscale" imaging using spectrum-integrating detectors. The ability to get spectrally differently weighted information from the same image view enables well-known and broadly discussed new diagnostic features, for example, material separation, material recognition, beam hardening correction, and quantitative imaging.

For spectral imaging the exact knowledge of the exposing X-ray spectrum is required. Even very small spectral variations, for example in the ratio between high energy and low energy X-ray photons, will cause severe artifacts in diagnostic features, like material separation.

Typically, an exact tube spectrum is measured during a calibration procedure, however there are many effects which influence a spectrum on a very short time scale and which cannot be accounted for during an actual imaging process. For example, the applied tube voltage might drift during the imaging procedure, or voltage ripples of different strengths might occur.

US2014/0014828A1 describes a method and system for adaptive calibration for tomographic imaging systems.

SUMMARY OF THE INVENTION

It would be advantageous to have an improved technique for determining the effective energy spectra of an X-ray tube during the specific time periods of X-ray image creation, thereby enabling the X-ray images to be corrected for temporal spectrum variations, or using the particular spectra directly for deriving particular object properties like e.g. material compositions or particular material concentrations of the examined object.

The object of the present invention is solved with the subject matter of the independent claims, wherein further embodiments are incorporated in the dependent claims. It should be noted that the following described aspects of the invention apply also for the apparatus for determining an effective energy spectrum of an X-ray tube, the system for determining object related quantities based on X-ray image data, the method for determining an effective energy spectrum of an X-ray tube, the method for determining an object related quantity based on X-ray image data, and the computer program element and the computer readable medium.

According to a first aspect, there is provided an apparatus for determining an effective energy spectrum of an X-ray tube, comprising:
an input unit; and
a processing unit.

The input unit is configured to provide the processing unit with a temporally varying acceleration voltage of an X-ray tube for a time period. The temporally varying acceleration voltage is provided at a temporal sampling frequency configured to resolve at least some temporally varying voltage ripples. The input unit is also configured to provide the processing unit with a temporally varying X-ray tube current for the time period. The temporally varying X-ray tube current is provided at a temporal sampling frequency configured to resolve at least some temporally varying current ripples. The processing unit is configured to determine at least one product of the temporally varying X-ray tube current and a time interval. The processing unit is also configured to determine an effective energy spectrum of the X-ray tube as a function of the at least one product of the temporally varying X-ray tube current and the time interval and as a function of the voltage of the X-ray tube.

In this manner, the effective energy spectrum of an X-ray tube can be determined for different time periods. In other words, over different time periods when the X-ray tube is being used in the acquisition of spectral X-ray images, the effective energy spectrum of the X-ray tube for each of those time periods can be determined. Then, if the characteristics of the X-ray tube varies such that the energy spectrum varies between different time periods, the effective energy spectra of the X-ray tube for those different time periods can be used to correct the acquired spectrally dependent X-ray images. To put this another way, by determining an effective energy spectrum of the X-ray tube, X-ray images acquired at different times when the X-ray tube is emitting X-rays with differing energy spectra can be corrected or normalised such that they will appear to have been acquired with an X-ray tube that has not changed its spectral output. Also, the X-ray images can be interpreted according to the correspondingly determined X-ray spectra such that further data processing steps reveal improved accuracy of particular object properties of interest.

In an example, the temporally varying acceleration voltage is provided at a temporal sampling frequency configured to resolve at least some temporally varying voltage ripples.

In an example, the temporally varying X-ray tube current is provided at a temporal sampling frequency configured to resolve at least some temporally varying current ripples.

In other words, temporal ripples in the voltage and current of the X-ray tube can be resolved and taken into account. In this manner, voltage and current ripples, that lead to an associated temporal change in the emitted spectrum of the X-ray tube, can be resolved and in this way the temporally changing spectrum of the X-ray tube output during image acquisition can be accounted for, enabling images to be appropriately corrected.

In an example, the temporally varying acceleration voltage and/or the temporally varying X-ray tube current are determined based on modelling In an example, the temporally varying acceleration voltage and/or the temporally varying tube current is derived by the measurement of correlated quantities.

In an example, over a time interval the temporally varying X-ray tube current has a discrete value and wherein over the time interval the temporally varying acceleration voltage has a discrete value, and wherein the at least one product is determined as the product of the discrete value of the X-ray tube current with the time interval and this product is associated with the discrete value of the acceleration voltage.

In this manner, continuously varying voltage and currents are set as discrete values, which can apply to time intervals of fixed duration, thereby enabling the effective energy spectrum to be determined.

In an example, the processing unit is configured to determine a histogram of the at least one product of the temporally varying X-ray tube current and the time interval as a function of the voltage of the X-ray tube, and wherein the processing unit is configured to determine the effective energy spectrum as a function of the histogram.

In this manner, a simplification in processing is provided. In an example, a histogram value is calculated for a voltage interval and the histogram value represents the sum of all X-ray tube currents multiplied by the time interval for which temporally varying voltages are found within that voltage interval. In other words, in an example the histogram is made up of a number of increasing voltage segments of specific voltage width, which need not be equal in voltage interval. For the first voltage interval, voltages within this interval may be present in the temporally varying acceleration voltage at an early time and a mid time and at a late time over the time period. For each of these acceleration voltages the associated X-ray tube current at the early, mid and late times is multiplied by the sampling time interval and summed together. This is then carried out for the second voltage interval, and the third voltage interval etc.

In this manner, at each time step through an exposure, where an acceleration voltage and associated X-ray tube current occurs, the appropriate histogram voltage bin is determined and only one addition (of the X-ray tube current) to the histogram value needs to be carried out in order that the effective energy spectrum of the X-ray tube can be generated. This is computationally efficient.

In an example, the processing unit is configured to determine the effective energy spectrum of the X-ray tube as a function of an X-ray tube spectrum function.

In an example, the input unit is configured to provide the processing unit with X-ray image data of an object acquired over an acquisition time period utilising X-rays generated from the X-ray tube; wherein, the processing unit is configured to determine an effective energy spectrum of the X-ray tube for the time of acquisition of the X-ray image data; wherein the processing unit is configured to determine at least one object related quantity as a function of the X-ray image data and as a function of the effective energy spectrum.

Here "X-ray image data" could be a single "X-ray attenuation" image but also a set of simultaneously acquired images, e.g. the photon count rates for particular energy intervals in the case of a energy separating photon counting detector.

In this manner, the accuracy of spectral X-ray image can be improved based on object related quantities which are derived from the image data.

In an example, the object related quantity is the image as it would be acquired for an X-ray tube having a reference spectrum, in which case it can be considered that the image has been "corrected".

In this manner a corrected spectral X-ray image can be determined as it would have been measured with an X-ray tube that emitted a constant reference energy spectrum. This means that all images that are acquired, can be corrected as if they had been acquired with an X-ray tube operating such that it produced a constant reference energy spectrum. To put this another way, the effects of variation of the output characteristics of the X-ray tube can be accounted for with respect to a particular X-ray tube, and different X-ray tubes can be corrected such that they all appear to be operating with a constant reference energy spectrum. In an example, the object related quantity is one of the following:

- X-ray image data as it would be acquired with a reference energy spectrum,
- X-ray image data as it would be acquired with monochromatic X-ray radiation;
- X-ray image data generated from weighted additions or subtractions of acquired image data referring to a reference spectrum or to monochromatic X-ray radiation;
- a two-dimensional or a three-dimensional representation of a property of the examined object, wherein the property is characterizing an object length, a mass density, a particular concentration of one material or a mix of materials, a quantity representing a mean atomic order of elements, a quantity representing X-ray attenuation, or a quantity representing an aspect of X-ray attenuation like attenuation from the photoelectric effect or from Compton scattering or from coherent scattering.

In an example, the processing unit is configured to determine at least one length through the object as a function of the effective energy spectrum.

In an example, the processing unit is configured to correct the X-ray image as a function of the at least one length through the object and as a function of a reference energy spectrum.

In an example, the processing unit is configured to determine at least one length through the object as a function of the X-ray image and as a function of at least one linear X-ray attenuation coefficient.

According to a second aspect, there is provided a system for determining object related quantities based on X-ray image data, the system comprising:

an image acquisition unit comprising an X-ray tube;
a voltage acquisition unit;
a current acquisition unit;
an apparatus for determining an effective energy spectrum of an X-ray tube according to the first aspect and any associated example; and
an output unit;

The image acquisition unit is configured to provide X-ray image data of an object to the input unit, wherein the X-ray image data is acquired over an acquisition time. The voltage acquisition unit is configured to provide the input unit with a temporally varying acceleration voltage of the X-ray tube during the acquisition time of the X-ray image data. The current acquisition unit is configured to provide the input unit with a temporally varying X-ray tube current during the acquisition time of the X-ray image data. The apparatus is configured to determine an effective energy spectrum of the X-ray tube for the time of acquisition of the X-ray image data. The processing unit is configured to determine at least one object related quantity as a function of the X-ray image data and as a function of the effective energy spectrum. The output unit is configured to output data representative of the object related quantity.

In an example, the processing unit is configured to determine at least one length through the object as a function of the effective energy spectrum.

In an example, the processing unit is also configured to correct the X-ray image as a function of the at least one length through the object and as a function of a reference energy spectrum.

In an example, output unit is configured to output data representative of the corrected X-ray image.

In a third aspect, there is provided a method for determining an effective energy spectrum of an X-ray tube, comprising:

a) providing a temporally varying acceleration voltage of an X-ray tube for a time period, wherein the temporally varying acceleration voltage is provided at a temporal sampling frequency configured to resolve at least some temporally varying voltage ripples;

b) providing a temporally varying X-ray tube current for the time period, wherein the temporally varying X-ray tube current is provided at a temporal sampling frequency configured to resolve at least some temporally varying current ripples;

c) determining at least one product of the temporally varying X-ray tube current and a time interval; and e) determining an effective energy spectrum of the X-ray tube as a function of the at least one product of the temporally varying X-ray tube current and the time interval and as a function of the voltage of the X-ray tube.

In a fourth aspect, there is provided a method for determining an object related quantity based on X-ray image data, the method comprising:

a) providing X-ray image data of an object, wherein the X-ray image data is acquired over an acquisition time;

b) providing a temporally varying acceleration voltage of the X-ray tube during the acquisition time of the X-ray image data, wherein the temporally varying acceleration voltage is provided at a temporal sampling frequency configured to resolve at least some temporally varying voltage ripples;

c) providing a temporally varying X-ray tube current during the acquisition time of the X-ray image data, wherein the temporally varying X-ray tube current is provided at a temporal sampling frequency configured to resolve at least some temporally varying current ripples;

d) determining at least one product of the temporally varying X-ray tube current and a time interval;

e) determining an effective energy spectrum of the X-ray tube for the time of acquisition of the X-ray image data, the effective energy spectrum being determined as a function of the at least one product of the temporally varying X-ray tube current and the time interval and as a function of the voltage of the X-ray tube;

f) determining at least one object related quantity as a function of the X-ray image data and as a function of the effective energy spectrum; and h) outputting of data representative of the object related quantity.

In an example, the method comprises the step g), correcting the X-ray image data as a function of the effective energy spectrum.

In an example, the method comprises determining at least one length through the object as a function of the effective energy spectrum, and correcting the X-ray image data as a function of the at least one length through the object and as a function of a reference energy spectrum.

In an example, the method comprises outputting of data representative of the corrected X-ray image data.

According to another aspect, there is provided a computer program element controlling apparatus as previously described which, in the computer program element is executed by processing unit, is adapted to perform the method steps as previously described.

According to another aspect, there is provided a computer readable medium having stored computer element as previously described.

Advantageously, the benefits provided by any of the above aspects and examples equally apply to all of the other aspects and examples and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
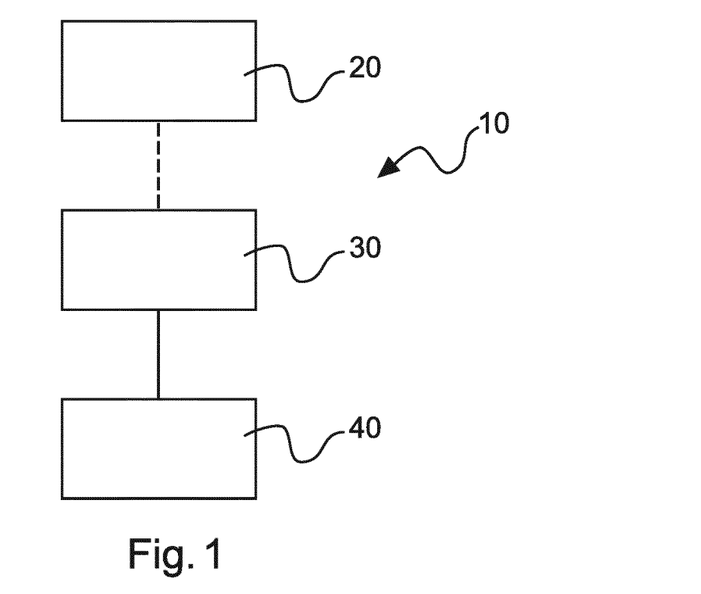
FIG. 1 shows a schematic set up of example of an apparatus for determining an effective energy spectrum of an X-ray tube.

FIG. 1 shows an apparatus 10 for determining an effective energy spectrum of an X-ray tube 20. The apparatus comprises an input unit 30 and a processing unit 40. The input unit 30 is configured to provide the processing unit 40 with a temporally varying acceleration voltage of an X-ray tube 20 for a time period. The input unit 30 is also configured to provide the processing unit 40 with a temporally varying X-ray tube current for the time period. The processing unit 40 is configured to determine at least one product of the temporally varying X-ray tube current and a time interval. The processing unit 40 is also configured to determine an effective energy spectrum of the X-ray tube as a function of the at least one product of the temporally varying X-ray tube current and the time interval and as a function of the voltage of the X-ray tube.

In the discussion that follows, a spectral X-ray image is an X-ray image acquired with a broadband X-ray source operating with a spectrally sensitive X-ray detector. In an example, the spectrally sensitive X-ray detector is a detector which provides the number of single X-ray detection events being counted above particular threshold energies for the X-ray photons, thereby enabling a counting of X-ray photons which are assigned to energy intervals between said particular threshold values. Therefore, determining the original number of photons emitted by the source in said energy intervals within a time period and comparing it with the number of measured photons after passing through an object to be examined it is possible to conclude about the spectrally dependent X-ray attenuation of the object which therefore allows conclusions on the material composition of the examined object. In other words, the detector can be a photon counting detector, which counts incident photons according to their belonging to an energy interval. To put this another way, a histogram distribution "number of counts" vs. "photon energy" is created by the detector.

According to an example, the temporally varying acceleration voltage is provided at a sampling frequency configured to resolve at least some temporally varying voltage ripples.

According to an example, the temporally varying X-ray tube current is provided at a sampling frequency configured to resolve at least some temporally varying current ripples.

In an example, a voltage acquisition unit is configured to acquire the temporally varying acceleration voltage of the X-ray tube.

In an example, a current acquisition unit is configured to acquire the temporally varying X-ray tube current.

To put this another way, direct measurements of the temporally varying acceleration voltage and of the temporally varying X-ray tube current with a sampling frequency high enough such that voltage and current ripples can be resolved can be conducted.

According to an example, the temporally varying acceleration voltage and/or the temporally varying X-ray tube current are determined based on modelling.

In an example, empirical data acquired as part of laboratory experiments on X-ray tubes is used to build a model or models from which the temporally varying acceleration voltage and the temporally varying X-ray tube current are determined.

According to an example, the temporally varying acceleration voltage and/or the temporally varying tube current is derived by the measurement of correlated quantities.

In an example, the temporally varying acceleration voltage and/or the temporally varying tube current is derived indirectly by measurement of the cathode emission current. In an example, the temporally varying acceleration voltage and/or the temporally varying tube current is derived indirectly by measurement of the time resolved X-ray flux.

According to an example, over the time interval the temporally varying X-ray tube current has a discrete value and wherein over the time interval the temporally varying acceleration voltage has a discrete value, and wherein the at least one product is determined as the product of the discrete value of the X-ray tube current with the time interval and this product is associated with the discrete value of the acceleration voltage.

In an example, the time period is divided into a number of time intervals of the same duration.

In this manner, continuously varying voltage and currents are set as discrete values, which can apply to time intervals of fixed duration, thereby enabling the effective energy spectrum to be determined.

According to an example, the processing unit is configured to determine a histogram of the at least one product of the temporally varying X-ray tube current and the time interval as a function of the voltage of the X-ray tube, and wherein the processing unit is configured to determine the effective energy spectrum as a function of the histogram.

In other words, in an example the histogram is made up of a number of increasing voltage segments of specific voltage width, which need not be equal in voltage interval. For the first voltage interval, voltages within this interval may be present in the temporally varying acceleration voltage at an early time and a mid time and at a late time over the time period. For each of these acceleration voltages the associated X-ray tube current at the early, mid and late times is multiplied by the sampling time interval and summed together. This is then carried out for the second voltage interval, and the third voltage interval etc. The following example helps to explain this, where in an example an acceleration voltage is set at 10 kV and the nominal X-ray tube current is set at 1 A. However, over time the following varying (voltage:current) pairings are directly measured or determined to occur through modelling or through derived measurements, where these lead to associated changes in the spectral output of the X-ray tube. In this example, the voltage (in units of e.g. kV) and current (in units of e.g. A) is varying about these nominal values in the following manner over time within a sampling time period: (10.05: 1.005), (9.82:0.982), (9.83:0.983), (10.01:1.001), (9.86: 0.986), (9.87:0.987), (10.06:1.006), (9.9:0.99), (9.8:0.98), (9.93:0.993), (9.95:0.995), (10.09:1.009), (9.97:0.997), (10.03:1.003), (10.07:1.007). Then for a constant time interval width $\Delta t$, the histogram value over the voltage range 9.8-9.849 equals $\Delta t \cdot (0.98+0.982+0.983)$, the histogram value over the voltage range 9.85-9.899 equals $\Delta t \cdot (0.986+0.987)$, the histogram value over the voltage range 9.9-9.949 equals $\Delta t \cdot (0.99+0.993)$, the histogram value over the voltage range 9.95-9.999 equals $\Delta t \cdot (0.995+0.997)$, the histogram value over the voltage range 10.0-10.049 equals $\Delta t \cdot (1.001+1.003)$, and the histogram value over the voltage range 10.05-10.099 equals $\Delta t \cdot (1.005+1.006+1.007+1.009)$.

In an example, the total number and width of the histogram bins is chosen such that the voltage variations during an X-ray exposure can be sampled with adequate resolution and range.

According to an example, the processing unit is configured to determine the effective energy spectrum of the X-ray tube as a function of an X-ray tube spectrum function.

In an example, the tube spectrum function represents the photons per energy bin emitted per unit time and unit tube current into a solid angle as a function of the X-ray energy. In an example, the tube spectrum function is determined through experimental calibration or by theoretical modelling. In other words, the tube spectrum function represents how the flux of the radiation of the X-ray tube varies as a function of energy for different fixed acceleration voltages.

In an example, the apparatus can be used in medical X-ray imaging or image display, for example the apparatus can be used in C-arm or CT X-ray image systems utilising spectral information within the X-rays. In an example, the apparatus can be used in non-medical X-ray imaging or image display, for example the apparatus can be used in non-destructive testing systems or in screening systems, e.g., airport luggage screening systems. In an example, the apparatus can be used in tomosynthesis imaging or image display. In an example, the apparatus can be used in breast tomosynthesis imaging or image display. In an example, the apparatus can be used in digital tomosynthesis imaging or image display.

The following is provided with respect to the term "spectral information": In currently used practice, "spectral information" means that (per spatial projection through the object) at least two measurement values are acquired, where each value is in an individual way dependent on the energy spectrum (each value can be considered as a spectrum integral with a particular weighting function). This has to be distinguished from "non-spectral information" where somewhat only a single (weighted) integral spectrum is determined in a single value. Today, most X-ray systems are "non-spectral". The apparatus described here has applicability to spectral and non-spectral systems. The apparatus has applicability to "non-spectral" systems because the acquired "one signal per projection" is still dependent on the spectrum. However, the applicability of the described apparatus is however more pronounced for the "spectral" systems, because of the explicit use of X-ray photons over the emitted energy range.

According to an example, the input unit is configured to provide the processing unit with X-ray image data of an object acquired over an acquisition time period utilising X-rays generated from the X-ray tube; wherein, the processing unit is configured to determine an effective energy spectrum of the X-ray tube for the time of acquisition of the X-ray image data; wherein the processing unit is configured to determine at least one object related quantity as a function of the X-ray image data and as a function of the effective energy spectrum.

According to an example, the object related quantity is one of the following:
- X-ray image data as it would be acquired with a reference energy spectrum,
- X-ray image data as it would be acquired with monochromatic X-ray radiation,
- X-ray image data generated from weighted additions or subtractions of acquired image data referring to a reference spectrum or to monochromatic X-ray radiation,
- a two-dimensional or a three-dimensional representation of a property of the examined object, wherein the property is characterizing an object length, a mass density, a particular concentration of one material or a mix of materials, a quantity representing a mean atomic order of elements, a quantity representing X-ray attenuation, or a quantity representing an aspect of X-ray attenuation like attenuation from the photoelectric effect or from Compton scattering or from coherent scattering.

According to an example, the input unit is configured to provide the processing unit with an X-ray image of an object acquired over an acquisition time utilising X-rays generated from the X-ray tube, and the processing unit is configured to determine an effective energy spectrum of the X-ray tube for the time of acquisition of the X-ray image. The processing unit is also configured to determine at least one length through the object as a function of the effective energy spectrum, and the processing unit is configured to correct the X-ray image as a function of the at least one length through the object and as a function of a reference energy spectrum.

In an example, the X-ray image data is an X-ray image.

In an example, the X-ray image data is a set of X-ray images acquired with different spectral weights.

In an example, the reference energy spectrum is an earlier effective spectrum determined for the X-ray tube. In an example, the reference energy spectrum is a standard "idealised" energy spectrum that can be applied to all similar X-ray tubes.

According to an example, the processing unit is configured to determine the at least one length through the object as a function of the X-ray image and as a function of at least one linear X-ray attenuation coefficient.

In an example, the object is assumed to consist of a uniform material (e.g. equal density water) and the at least one length through the object is at least one accumulated length of water segments on the X-ray path through the object. In an example, the object is assumed to be characterised by a linear X-ray attenuation coefficient (e.g. that of water). In this manner, the acquired spectral X-ray image and the determined effective energy spectrum of the X-ray tube (along with a known or assumed spectral sensitivity of the detector) can be used to determine the length values through the object. The length values can then be used with the reference energy spectrum of an X-ray tube to correct the spectral X-ray image to create an image that would have been acquired had the X-ray tube been operating with that constant reference energy spectrum.

Figure 2:
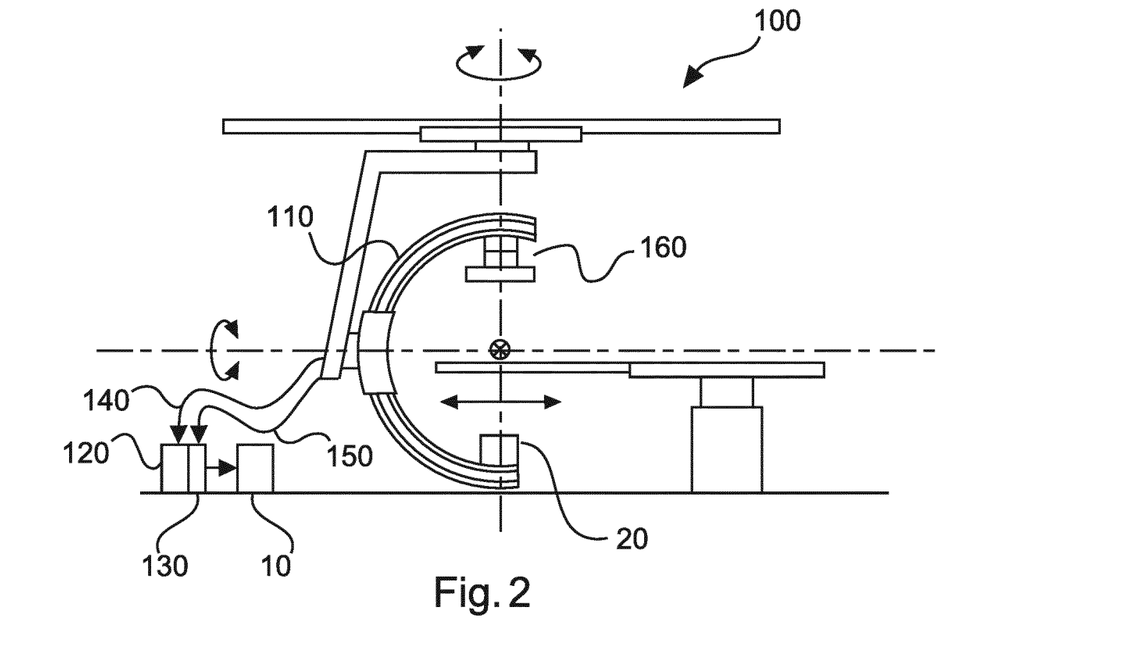
FIG. 2 shows a schematic set up of an example of a system for determining an object related quantity based on X-ray image data.

FIG. 2 shows a system 100 for determining object related quantities based on X-ray image data. The system 100 comprises an image acquisition unit 110 comprising an X-ray tube 20, a voltage acquisition unit 120, a current acquisition unit 130, an apparatus 10 for determining an effective energy spectrum of an X-ray tube according to the apparatus described with reference to FIG. 1, and an output unit (not shown). The image acquisition unit 110 has an X-ray image detector 160 opposing the X-ray tube 20, and mechanical means are provided to position the X-ray image detector 160 and the X-ray tube 160 around an object. Communication cables 140 and 150 are shown running between the image acquisition unit 110 and the voltage acquisition unit 120 and current acquisition unit 130 respectively, and then to the apparatus 10. However, communication cabling can also be provided from the image acquisition unit 110 to the apparatus 10 directly. The image acquisition unit 110 is configured to provide X-ray image data (e.g. an X-ray image) of the object to the input unit 30 of the apparatus 10, wherein the X-ray image data is acquired over an acquisition time. The voltage acquisition unit 120 is configured to provide the input unit 30 with a temporally varying acceleration voltage of the X-ray tube 20 during the acquisition time of the X-ray image data. The current acquisition unit 130 is configured to provide the input unit 30 with a temporally varying X-ray tube current, of the X-ray tube 20, during the acquisition time of the X-ray image data. The apparatus 10 is configured to determine an effective energy spectrum of the X-ray tube 20 for the time of acquisition of the X-ray image data. The processing unit 40, of the apparatus 10, is configured to determine at least one object related quantity as a function of the X-ray image data and as a function of the effective energy spectrum. The output unit 160 (not shown) is configured to output data representative of the object related quantity (e.g. a corrected X-ray image).

In an example, the processing unit 40 is configured to determine at least one length through the object as a function of the effective energy spectrum.

In an example, the processing unit 40 is configured to correct the X-ray image as a function of the at least one length through the object and as a function of a reference energy spectrum.

In an example, the image acquisition unit comprises an X-ray imaging device, for example, a C-arm arrangement, or a CT arrangement or tomosynthesis arrangement.

Figure 3:
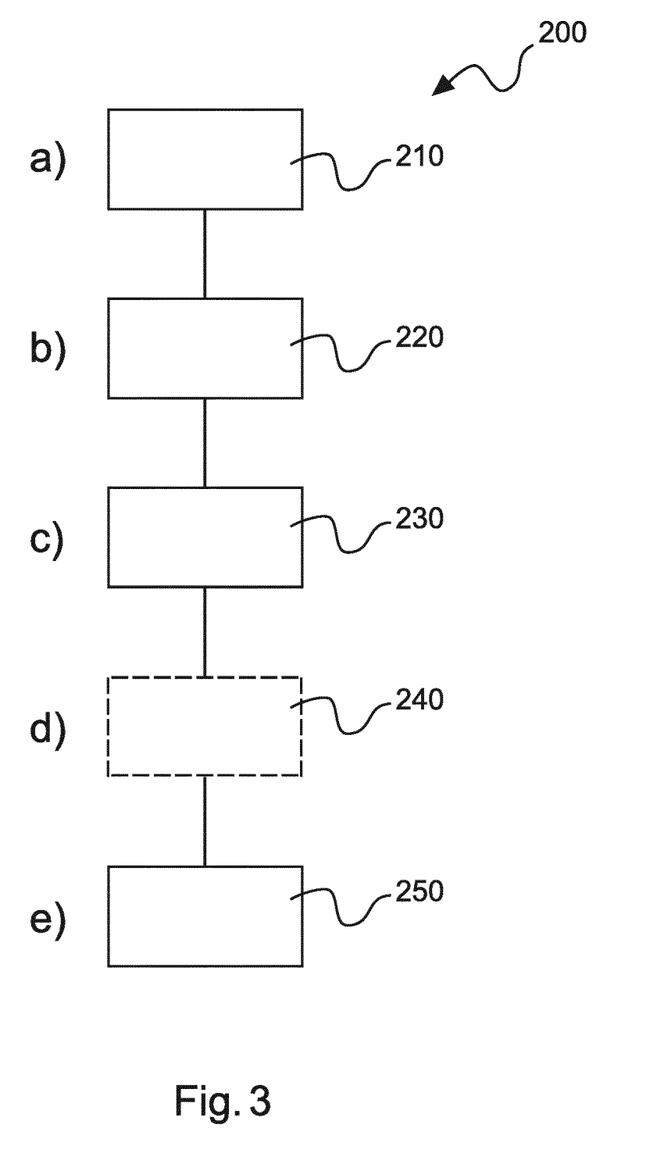
FIG. 3 shows a method for determining an effective energy spectrum of an X-ray tube.

FIG. 3 shows a method 200 for determining an effective energy spectrum of an X-ray tube in its basic steps. The method comprises the following:

In a first providing step 210, also referred to as step a), a temporally varying acceleration voltage of an X-ray tube is provided for a time period.

In a second providing step 220, also referred to as step b), a temporally varying X-ray tube current is provided for the time period.

In a first determining step 230, also referred to as step c), at least one product of the temporally varying X-ray tube current and a time interval is determined.

In a second determining step 250, also referred to as step e), an effective energy spectrum of the X-ray tube is determined as a function of the at least one product of the temporally varying X-ray tube current and the time interval and as a function of the voltage of the X-ray tube.

In an example, the temporally varying acceleration voltage is provided at a temporal sampling frequency configured to resolve at least some temporally varying voltage ripples. In an example, the temporally varying X-ray tube current is provided at a temporal sampling frequency configured to resolve at least some temporally varying current ripples. In an example, the temporally varying acceleration voltage and the temporally varying X-ray tube current are determined based on modelling. In an example, the temporally varying acceleration voltage and/or the temporally varying tube current is derived by the measurement of correlated quantities.

In an example, over the time interval the temporally varying X-ray tube current has a discrete value and wherein over the time interval the temporally varying acceleration voltage has a discrete value, and wherein the at least one product is determined as the sum of the discrete value of the X-ray tube current with the time interval and this sum is associated with the discrete value of the acceleration voltage.

In an example, the method comprises step d) determining 240 a histogram of the at least one product of the temporally varying X-ray tube current and the time interval as a function of the voltage of the X-ray tube, and wherein step e) comprises determining the effective energy spectrum as a function of the histogram.

In an example, step e) comprises determining the effective energy spectrum of the X-ray tube as a function of an X-ray tube spectrum function.

In an example, the method comprises providing an X-ray image of an object acquired over an acquisition time utilising X-rays generated from the X-ray tube. The method also comprising determining an effective energy spectrum of the X-ray tube for the time of acquisition of the X-ray image, and determining at least one length through the object as a function of the effective energy spectrum. The method also comprises correcting the X-ray image as a function of the at least one length through the object and as a function of a reference energy spectrum.

In an example, the method comprises determining the at least one length through the object as a function of the X-ray image and as a function of at least one linear X-ray attenuation coefficient.

Figure 4:
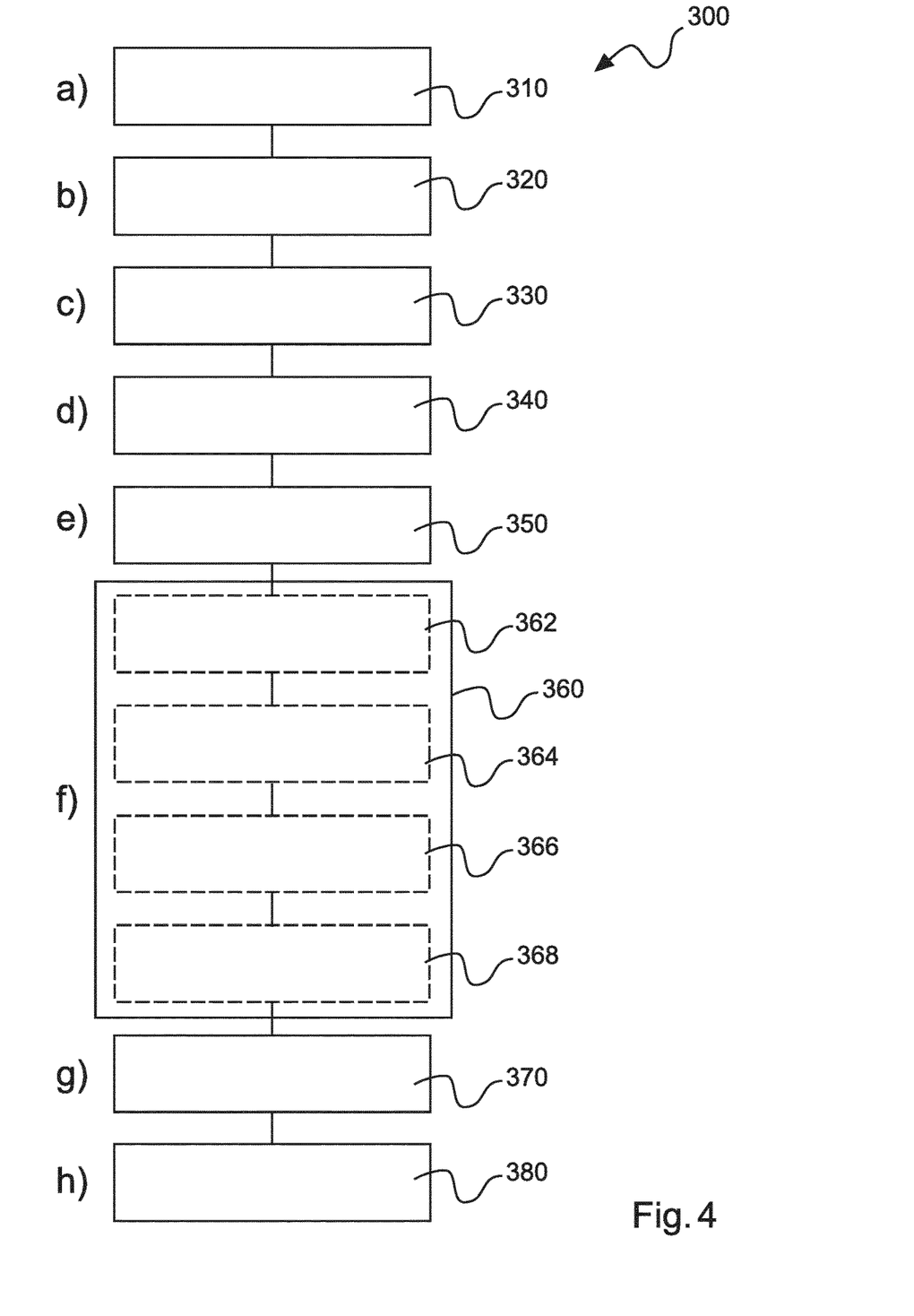
FIG. 4 shows a method for determining an object related quantity based on X-ray image data.

FIG. 4 shows a method for determining an object related quantity based on X-ray image data in its basic steps. The method comprises the following:

In a first providing step 310, also referred to as step a), X-ray image data of an object is provided, wherein the X-ray image data is acquired over an acquisition time.

In a second providing step 320, also referred to as step b), a temporally varying acceleration voltage of the X-ray tube during the acquisition time of the X-ray image data is provided.

In a third providing step 330, also referred to as step c), a temporally varying X-ray tube current during the acquisition time of the X-ray image data is provided.

In a first determining step 340, also referred to as step d), at least one product of the temporally varying X-ray tube current and a time interval is determined.

In a second determining step 350, also referred to as step e), an effective energy spectrum of the X-ray tube for the time of acquisition of the X-ray image data is determined, the effective energy spectrum being determined as a function of the at least one product of the temporally varying X-ray tube current and the time interval and as a function of the voltage of the X-ray tube.

In a third determining step 360, also referred to as step f), at least one object related quantity is determined as a function of the X-ray image data and as a function of the effective energy spectrum.

In an outputting step 380, also referred to as step h), data representative of the object related quantity is output.

In an example, the method comprises a correcting step 370, also known as step g), where the X-ray image data is corrected as a function of the effective energy spectrum.

In an example, at least one length through the object is determined as a function of the effective energy spectrum, and step g) comprises correcting the X-ray image data as a function of the at least one length through the object and as a function of a reference energy spectrum.

In an example, data representative of the corrected X-ray image is output.

In an example, determining 360 at least one length through the object comprises, utilisation 362 of the attenuation values in the X-ray image. In an example, determining 360 at least one length through the object comprises, utilisation 364 of a known detector spectral sensitivity. In an example, determining 360 at least one length through the object comprises, utilisation 366 of spectral linear X-ray attenuation coefficients of a known material. In an example, determining 360 at least one length through the object comprises, utilisation 368 of spectral linear X-ray attenuation coefficients of water.

Figure 5:
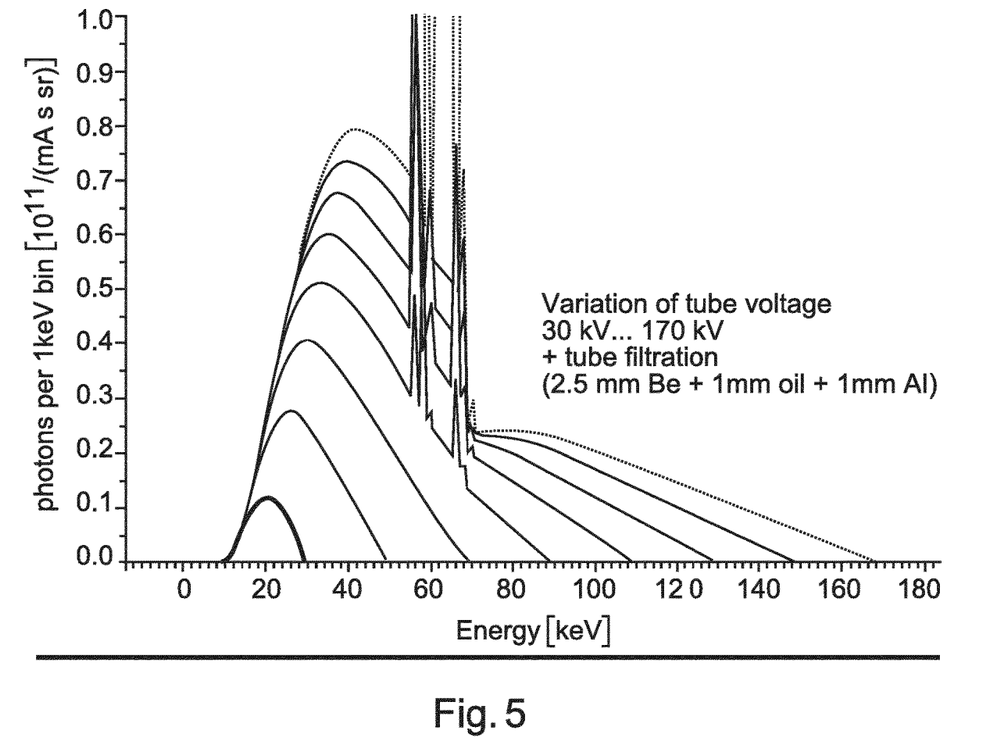
FIG. 5 shows an example of modeled X-ray spectra for different X-ray tube acceleration voltages between 30 and 170 kV.

FIG. 5 shows an example of modeled X-ray spectra for different X-ray tube acceleration voltages between 30 and 170 kV. To understand in more detail the technique by which the effective energy spectrum of an X-ray tube is determined enabling spectral X-ray images to be corrected, the X-ray generation process is reviewed, which refers to the energy spectra shown in FIG. 5. X-ray tubes consist of a cathode which is emitting electrons, for typical medical applications with currents up to 1 A. The electrons are accelerated in an electric field towards the anode target, typically (but not restricted to) a rotating disc covered with a material of high atomic order, like e.g. tungsten or molybdenum. Typical acceleration voltages for medical imaging range from 10 kV up to 150 kV. Correspondingly, the free electrons reach a kinetic energy between 10 keV and 150 keV when hitting the anode target. In the target, the electrons interact with the target matter and partially generate X-ray photons. The energy spectrum of these photons accords to the very well-known "Bremsspectrum", as referred to in literature, enriched by peaks of characteristic radiation with well-defined energies. However, the Bremsspectrum radiation is sensitively dependent on the acceleration voltage as shown in FIG. 5.

Characteristically, the highest possible energy of an X-ray photon corresponds to the energy of the incident electrons, e.g. for 100 kV acceleration voltage the spectrum cuts off at exactly 100 keV X-ray photon energy. In contrast to the acceleration voltage, other X-ray tube parameters like the electron collection current from the anode (in the following abbreviated by "tube current") and the exposure time do not affect the spectral distribution function but scale linearly the X-ray flux, i.e. the number of photons for each energy. In particular, the X-ray flux $dN(E, V, J, t, \Omega)/dt$ dependence on photon energy E, acceleration voltage V, tube current J, time t, and X-ray emission (polar) angle $\Omega$ can be written as $$\frac{dN(E, V, J, t, \Omega)}{dt \cdot d\Omega} = J(t) \cdot f(E, V(t), \Omega)$$

where J(t) and V(t) indicate the tube current J and the acceleration voltage V as a function of time, and f indicates a tube spectrum function, for example as shown in FIG. 5.

To determine the energy-resolved total number N(E) of photons which are received, for example by an X-ray detector element placed in space, the photon flux needs to be integrated over space and time, i.e.

$$N(E) = \int_{t_1}^{t_2} dt \cdot J(t) \cdot \left( \int_{\Delta\Omega} d\Omega \cdot f(E, V(t), \Omega) \right) = \int_{t_1}^{t_2} dt \cdot J(t) \cdot F(E, V(t))$$

where [$t_1$, $t_2$] indicate the interval of X-ray exposure (i.e. with $t_2-t_1$ being the detector image acquisition time), and $\Delta\Omega$ being the solid angle spanned by the X-ray source and the detection area.

In the following, formula notation is simplified by assuming a spatially fixed source/detector position such that the space integration is replaced by a "tube spectrum function" F(E, V(t)). This latter function F is assumed to be known for all E and V, either by experimental calibration or by theoretical modeling, for example as shown in FIG. 5.

Looking at the latter formula it is clear that the (spectrally) resolved photon numbers received by the detector are a non-trivial function of time if J and/or V are non-constant. For every X-ray tube this is practically the case, even if a constant acceleration voltage and/or tube current is anticipated to be provided. This is because "voltage ripples" are present on the acceleration voltage, even if the acceleration voltage is considered to be stable. In other words, any constant voltage actually refers to an average tube voltage, and around that average there are significant high-frequency modulations up to the MHz regime occurring, with "arbitrary" amplitudes which are dependent on the quality of the high voltage generator. To put this another way, the acceleration voltage is not actually constant in time, but varies at frequencies up to the MHz scale around an average voltage.

Therefore, referring back to FIG. 5 as the acceleration voltage varies, the spectrum of X-ray energy emitted by the X-ray tube varies in amplitude, the highest emitted energy varies, the peak energy emitted varies, and specific peak emission characteristics vary. In other words, the whole energy spectrum varies as a function of the acceleration voltage, which as discussed above even for what is considered to be a constant voltage will suffer from voltage ripples where as the voltage ripples, the spectrum varies.

Therefore, N(E), relating to a real X-ray tube with varying characteristics, is actually representative of an effective spectrum which includes a weighted sum of spectra F(E, V) for different (constant) voltages V. In other words, as the acceleration voltage varies the actual emitted energy spectrum over a time period will be a sum of all the slightly different energy spectra representative of slightly different acceleration voltages. This leads to a cut off for the highest energy in a spectrum that is not sharply defined, but smoothed out and the integral X-ray intensity is non-linearly dependent on the voltage ripple amplitude. This non-linearity means that even for same "average" tube voltages different total X-ray intensities are observed for different ripple amplitudes about that average.

The situation becomes even more complex if the X-ray flux is not provided quasi-continuously but by means of pulses for V(t) and/or J(t) occurring during a detector sample time, as also rising and falling edges of the pulse(s) contribute to the total X-ray exposure.

To get an effective spectrum, enabling correction for energy spectrum variations, as compared to using an average for V and J, the time dependencies V(t) and 1(t) need to be determined.

One possibility is to model these quantities, for example based on empirical findings of laboratory experiments. In practice however this is a complex task and often the available information is not sufficient to get to acceptable results.

However, the direct measurement of the functions V(t) and J(t), with a temporal sampling frequency high enough such that voltage and current ripples can be resolved, also enables the effective spectrum to be determined. In other words, appropriate high frequency voltage and current acquisition or measurement units are used. In that case, the continuous functions become a series of discrete values $V_i$ and $J_i$ sampled at a time $t_i$, preferentially in equidistant time intervals of width $\Delta t$. In this case the above integral can be written in a discrete form of a sum $$N(E) = \Delta t \cdot \sum_i J_i \cdot F(E, V_i)$$

In practice, if the functions V(t) and J(t) are sampled with high frequency, a problem can occur either with high data amounts to be stored, or with high data processing efforts if said sum is calculated directly by a processing unit. Therefore, in this manner with suitable acquisition of voltages and currents, the energy spectrum variations of an X-ray tube can be determined, enabling the derivation of object related quantities dependent on the X-ray spectrum with higher accuracy as compared to the case that only an time-average spectrum is assumed.

Figure 6:
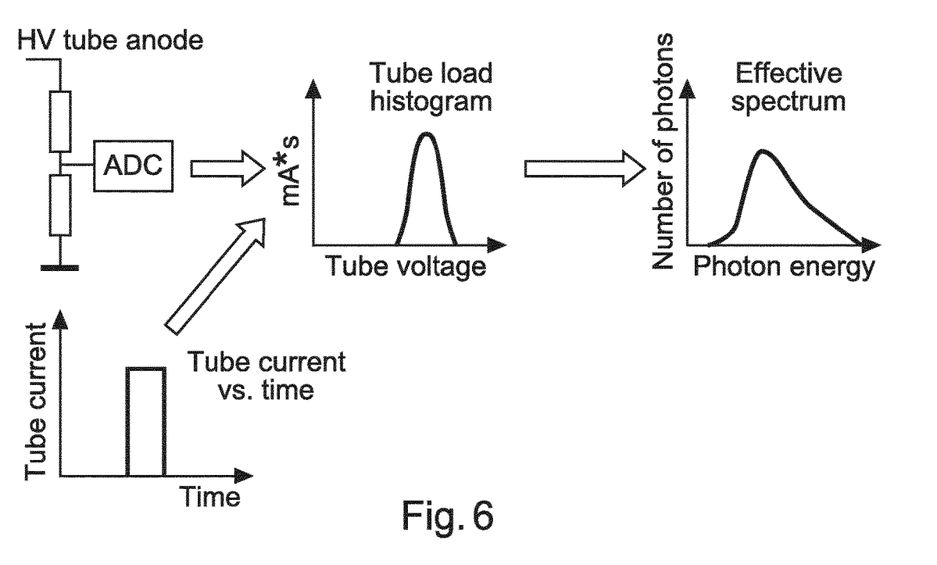
FIG. 6 shows a schematic representation of a detailed workflow for determining an effective spectrum for an X-ray tube.

FIG. 6 represents a detailed workflow of how, in a particular example, a simplification of the process enables an effective spectrum to be determined. The simplification of the processing effort is possible, if the time series is not stored completely, but instead a histogram of the sampled values is created. An exemplar "Tube load histogram" is shown in FIG. 6. In this case, the histogram value $h_k$ represents the sum of all currents $J_i$ for which the sampled voltage $V_i$ is found within a small voltage interval $\Delta V$ around an assigned voltage $V_k$. The total number and width of the histogram bins can be chosen such that the voltage variations during an X-ray exposure can be sampled with adequate resolution and range. In detail, the histogram sampling works as following: Initialize the histogram by setting $h_k$=0 for all k.

At a time $t_i$, sample a pair $V_i$ and $J_i$.

For the measured $V_i$, find a histogram index k.

Add the value $J_i$ to the k-th histogram bin $h_k$.

Each k is represented by a spectrum $F_k(E)=F(E, V_k)$, and with defining $k_i$ as the bin index belonging to the measured voltage $V_i$ we find $$N(E) = \Delta t \cdot \sum_k h_k \cdot F_k(E) \text{ with } h_k = \sum_{k=k_i} J_i$$

Here, constant sample time intervals $\Delta t$ are assumed, however also varying time intervals $\Delta t_i$ can be used in a more general formula $$N(E) = \sum_k h_k \cdot F_k(E) \text{ with } h_k = \sum_{k=k_i} J_i \cdot \Delta t_i$$

The advantage of the histogram method is that for each time step only one addition has to be performed and for each detector exposure only the final histogram array has to be stored to allow a derivation of the X-ray spectrum to a later time.

In other words, referring to FIGS. 5 and 6, the histogram in FIG. 6 indicates how often or how many times over an image acquisition period particular acceleration voltages of the X-ray tube were present, and referring to FIG. 5 the shape of the energy spectra for that voltage is known. Then for each voltage bin of the histogram, the associated slightly different energy spectrum is known. These can then be added together, but weighted by the tube current×time (the height of the histogram) for that voltage bin, because as discussed earlier the current does not change the shape of the spectrum at a fixed voltage only its intensity.

Image Correction

Figure 7:
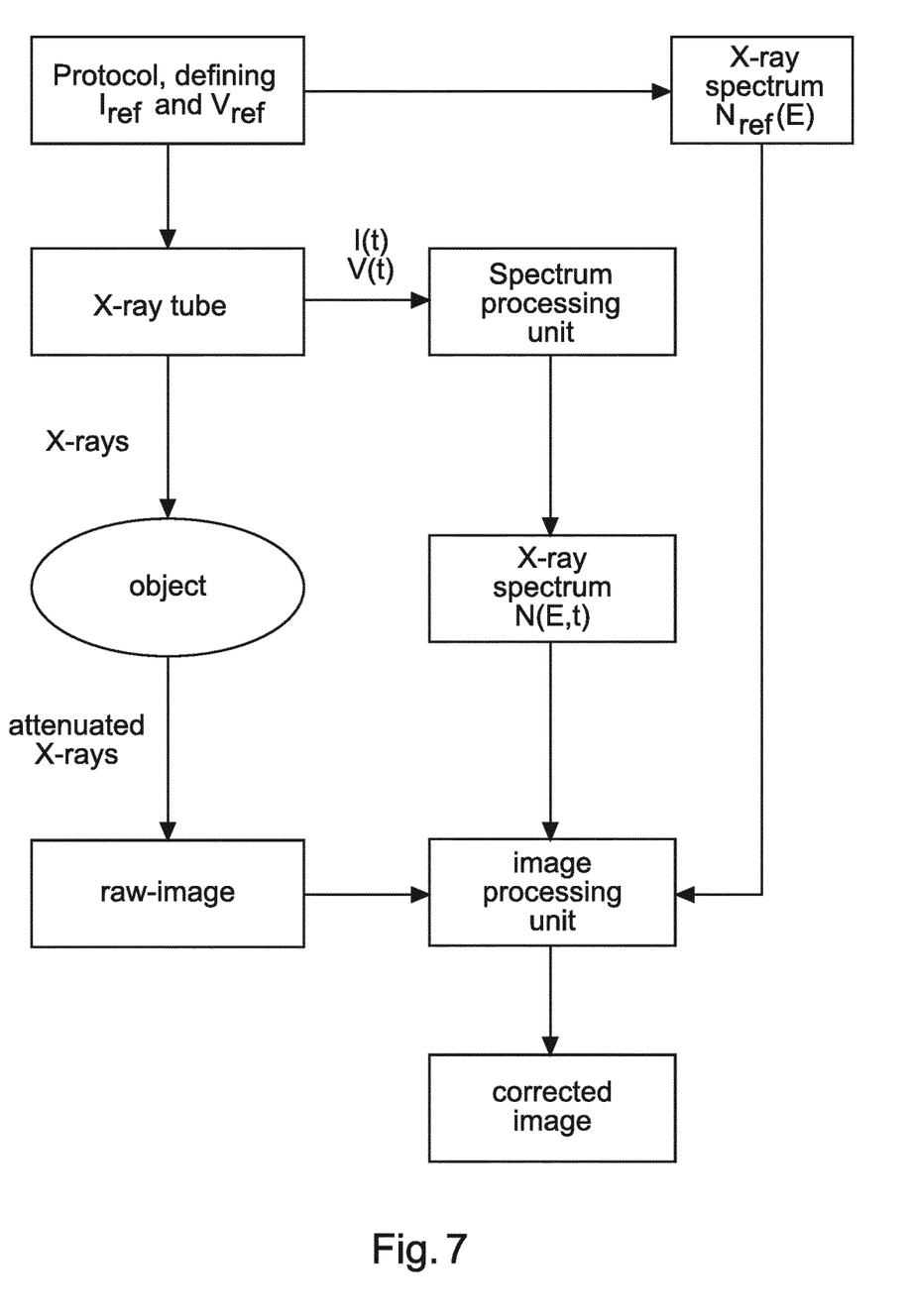
FIG. 7 shows a schematic representation of image correction.

To demonstrate how a better knowledge of the X-ray spectrum can be used in correcting images, we consider how the signal is generated with an object to be examined within the X-ray beam. It has to be said that it is out of scope of this document to review all the possible (spectrally sensitive) image acquisition methods as well as their current corrections, so we refer to state-of-the-art literature and here describe one specific example case. A very general formula for X-ray signal acquisition is $$S = \int_0^\infty dE \cdot N(E) \cdot D(E) \cdot A(E)$$

where S denotes the signal for a particular detector pixel (for the whole image, we need to add indices indicating which pixel is considered, which will be skipped in the following), N(E) is the effective spectrum emitted by the tube (as indicated in the prior section), D(E) is the spectral detector sensitivity, i.e. a weighting function describing the efficiency with which photons at energy E contribute to the signal, and A(E) is the object attenuation function.

For example, for an ideal energy integrating detector (e.g. a scintillator detector), D(E)=E is assumed indicating that the whole energy of a photon is converted into a signal. For an ideal photon counting detector, D(E)=1 is assumed. For an ideally energy discriminating photon counting detector, not one but several signals $S_i$ are generated where each signal $S_i$ has its individual spectral sensitivity function $D_i(E)$ which is a rectangular function, i.e. $D_i(E)$=1 if E is within a considered energy interval and $D_i(E)$=0 if E is outside the considered energy interval.

The object attenuation function is a complex function of material arrangement inside the object. Assuming that the path of an X-ray beam is parametrized by a path $\vec{r}(z)$, it can be described by $$A(E) = \exp\left(-\int dz \cdot \left|\frac{d\vec{r}}{dz}\right| \cdot \mu(\vec{r}(z), E)\right)$$

where $\mu(\vec{r}(z), E)$ is the energy dependent linear X-ray attenuation coefficient along the path $\vec{r}(z)$.

Now, let us consider a simplification assuming that the object consists of equal-density water, so the exponential integral can be simplified to $$\int dz \cdot \left|\frac{d\vec{r}}{dz}\right| \cdot \mu(\vec{r}(z), E) = \mu(E) \cdot L,$$

where μ(E) is the linear X-ray attenuation coefficient of water, and L is the accumulated length of the water segments on the X-ray path, so the attenuation function becomes $$A(E) = \exp(-\mu(E) \cdot L)$$

and the acquired X-ray signal becomes $$S = \int_0^\infty dE \cdot N(E) \cdot D(E) \cdot \exp(-\mu(E) \cdot L)$$

Without usage of the here discussed invention, N(E) is assumed to be a static reference spectrum creating a constant signal S (named $N_{ref}(E)$ and $S_{ref}$ in the following). However, an actually measured effective spectrum (named $N_{meas}(E)$ in the following) might be corrupted e.g. by means of varying ripple voltage such that we can write $N_{meas}(E, t) = N_{ref}(E) + \Delta N(E, t)$ where $\Delta N(E, t)$ symbolize the temporal variations of the spectrum. Therefore an actual measured signal becomes $$S(t) = \int_0^\infty dE \cdot N_{meas}(E, t) \cdot D(E) \cdot \exp(-\mu(E) \cdot L) =$$
$$\int_0^\infty dE \cdot N_{ref}(E) \cdot D(E) \cdot \exp(-\mu(E) \cdot L) +$$
$$\int_0^\infty dE \cdot \Delta N(E, t) \cdot D(E) \cdot \exp(-\mu(E) \cdot L) = S_{ref} + \Delta S(t)$$

As can be seen, as for the spectrum, the signal also becomes time dependent with a variation $\Delta S(t)$. Without knowledge of the quantity $\Delta N(E, t)$, the result would be not correctable and cause additional noise in the image acquisition.

With the here proposed invention, the actual effective spectrum $N_{meas}(E, t)$ (and thus the temporal spectrum variations $\Delta N(E, t)$) can be measured and used for correction purposes such that for example an image is created as it would be measured with a constant reference spectrum $N_{ref}(E)$.

For this, a two-step method can be applied, assumed that D(E) is known e.g. from detector calibration and μ(E), here from the material water, is taken from literature well-known by those skilled in the art.

Step 1: For a measured value $S_{meas}$, determine the water thickness L by numerically solving the equation $$S_{meas}(t) = \int_0^\infty dE \cdot N_{meas}(E, t) \cdot D(E) \cdot \exp(-\mu(E) \cdot L)$$

(here it helps that S(t) is a strictly monotonous function with respect to L).

Step 2: Use the determined value of L together with the defined reference spectrum $N_{ref}(E)$ to calculate a corrected value $S_{corr}$ using $$S_{corr}(t) = \int_0^\infty dE \cdot N_{ref}(E) \cdot D(E) \cdot \exp(-\mu(E) \cdot L)$$

A graphical representation of image correction is shown in FIG. 7.

To summarise the simplified example above, a device and method is provided which produces a histogram of tube voltages applied during the acquisition of a particular image frame this histogram is used to derive an effective X-ray exposure spectrum, which can be used for correction of acquired spectral images.

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A method for determining an effective energy spectrum of an X-ray tube, comprising:
   providing a temporally varying acceleration voltage of the X-ray tube for a predetermined time period that is divided into a predetermined number of time intervals, wherein the temporally varying acceleration voltage is provided at a first temporal sampling frequency configured to resolve at least some temporally varying voltage ripples;
   providing a temporally varying current of the X-ray tube for the predetermined time period, wherein the temporally varying current is provided at a second temporal sampling frequency configured to resolve at least some temporally varying current ripples;
   determining at least one result as a first function of the temporally varying current and a time interval; and
   determining an effective energy spectrum of the X-ray tube as a second function of the at least one result and the temporally varying acceleration voltage.

2. A method for determining an object related quantity based on X-ray image data, the method comprising:
   providing the X-ray image data of an object over a predetermined acquisition time that is divided into a predetermined number of time intervals;
   providing a temporally varying acceleration voltage of the X-ray tube during the predetermined acquisition time of the X-ray image data, wherein the temporally varying acceleration voltage is provided at a first temporal sampling frequency configured to resolve at least some temporally varying voltage ripples;
   providing a temporally varying current of the X-ray tube during the predetermined acquisition time of the X-ray image data, wherein the temporally varying current is provided at a second temporal sampling frequency configured to resolve at least some temporally varying current ripples;
   determining at least one result as a first function of the temporally varying current and a time interval;
   determining an effective energy spectrum of the X-ray tube as a second function of the at least one result and the temporally varying acceleration voltage;
   determining at least one object related quantity as a function of the X-ray image data and the effective energy spectrum; and outputting of data representative of the at least one object related quantity.

3. An apparatus for determining an effective energy spectrum of an X-ray tube, comprising:
an input unit configured to provide a temporally varying acceleration voltage of the X-ray tube for a predetermined time period that is divided into a predetermined number of time intervals, the temporally varying acceleration voltage being provided at a first temporal sampling frequency configured to resolve at least some temporally varying voltage ripples, the input unit being further configured to provide a temporally varying current of the X-ray tube for the predetermined time period, the temporally varying current being provided at a second temporal sampling frequency configured to resolve at least some temporally varying current ripples; and
a processing unit configured to determine at least one result as a first function of the temporally varying current and a time interval, the processing unit being further configured to determine an effective energy spectrum of the X-ray tube as a second function of the at least one result and the temporally varying acceleration voltage.

4. The apparatus according to claim 3, wherein at least one of the temporally varying acceleration voltage and the temporally varying current is determined based on modelling.

5. The apparatus according to claim 3, wherein at least one of the temporally varying acceleration voltage and the temporally varying current is derived by a measurement of correlated quantities.

6. The apparatus according to claim 3, wherein over the time interval the temporally varying current has a first discrete value, wherein over the time interval the temporally varying acceleration voltage has a second discrete value, wherein the at least one result is determined as a sum of the first discrete value of the temporally varying current and the time interval, and wherein the at least one result is associated with the second discrete value of the temporally varying acceleration voltage.

7. The apparatus according to claim 3, wherein the processing unit is configured to determine a histogram of the at least one result as a function of the temporally varying acceleration voltage, and wherein the processing unit is configured to determine the effective energy spectrum as a function of the histogram.

8. The apparatus according to claim 3, wherein the processing unit is configured to determine the effective energy spectrum of the X-ray tube as a function of an X-ray tube spectrum function.

9. The apparatus according to claim 3, wherein, the input unit is configured to provide the processing unit with X-ray image data of an object acquired over an acquisition time period using X-rays generated from the X-ray tube;
wherein the processing unit is configured to determine an effective energy spectrum of the X-ray tube for the acquisition time period of the X-ray image data;
wherein the processing unit is configured to determine at least one object related quantity as a function of the X-ray image data and as a function of the effective energy spectrum.

10. A system for determining object related quantities based on X-ray image data, the system comprising:
an image acquisition unit configured to provide the X-ray image data of an object acquired over a predetermined acquisition time;
a voltage acquisition unit configured to provide a temporally varying acceleration voltage of an X-ray tube during the predetermined acquisition time of the X-ray image;
a current acquisition unit configured to provide a temporally varying current of the X-ray tube during the predetermined acquisition time of the X-ray image data;
an apparatus for determining an effective energy spectrum of an X-ray tube, comprising:
an input unit configured to provide a temporally varying acceleration voltage of the X-ray tube for the predetermined acquisition time that is divided into a predetermined number of time intervals, the temporally varying acceleration voltage being provided at a first temporal sampling frequency configured to resolve at least some temporally varying voltage ripples, the input unit being further configured to provide a temporally varying current of the X-ray tube for the predetermined acquisition time, the temporally varying current being provided at a second temporal sampling frequency configured to resolve at least some temporally varying current ripples; and
a processing unit configured to determine at least one result as a first function of the temporally varying current and a time interval, the processing unit being further configured to determine an effective energy spectrum of the X-ray tube as a second function of the at least one result and the temporally varying acceleration voltage;
wherein the apparatus is configured to determine the effective energy spectrum of the X-ray tube for the predetermined acquisition time of the X-ray image data;
wherein the processing unit is configured to determine at least one object related quantity as a function of the X-ray image data and the effective energy spectrum; and
an output unit configured to output data representative of the at least one object related quantity.

11. A non-transitory computer-readable medium having one or more executable instructions stored thereon, which when executed by a processor, cause the processor to perform a method for determining an effective energy spectrum of an X-ray tube, the method comprising:
providing a temporally varying acceleration voltage of the X-ray tube for a predetermined time period that is divided into a predetermined number of time intervals, wherein the temporally varying acceleration voltage is provided at a first temporal sampling frequency configured to resolve at least some temporally varying voltage ripples;
providing a temporally varying current of the X-ray tube for the predetermined time period, wherein the temporally varying current is provided at a second temporal sampling frequency configured to resolve at least some temporally varying current ripples;
determining at least one result as a first function of the temporally varying current and a time interval; and
determining an effective energy spectrum of the X-ray tube as a second function of the at least one result and the temporally varying acceleration voltage.

* * * * *